United States Patent
Hughes et al.

(10) Patent No.: US 9,007,589 B2
(45) Date of Patent: Apr. 14, 2015

(54) CO-LOCATED POROSITY AND CALIPER MEASUREMENT FOR MEMBRANES AND OTHER WEB PRODUCTS

(71) Applicants: Michael Kon Yew Hughes, Vancouver (CA); Sebastien Tixier, North Vancouver (CA); Stuart James Heath, Surrey (CA)

(72) Inventors: Michael Kon Yew Hughes, Vancouver (CA); Sebastien Tixier, North Vancouver (CA); Stuart James Heath, Surrey (CA)

(73) Assignee: Honeywell ASCa Inc., Mississauga (CA)

( * ) Notice: Subject to any disclaimer, the term of this patent is extended or adjusted under 35 U.S.C. 154(b) by 74 days.

(21) Appl. No.: 14/027,883

(22) Filed: Sep. 16, 2013

(65) Prior Publication Data

US 2015/0077738 A1   Mar. 19, 2015

(51) Int. Cl.
*G01B 11/06* (2006.01)
*G01N 15/08* (2006.01)
*D21F 7/06* (2006.01)
*B65H 20/10* (2006.01)

(52) U.S. Cl.
CPC ........ *G01B 11/0691* (2013.01); *G01N 15/0826* (2013.01); *D21F 7/06* (2013.01); *B65H 20/10* (2013.01)

(58) Field of Classification Search
CPC ............... G01B 11/06; G01B 11/0691; G01N 2021/8609; G01N 2021/8645; G01N 33/346; G01N 15/08–15/0893; G01N 21/86; D21F 7/06; B65H 1/24; B65H 18/26; B65H 20/10; B65H 2515/34; B65H 2515/342

USPC .......................................................... 356/429
See application file for complete search history.

(56) References Cited

U.S. PATENT DOCUMENTS

| | | | |
|---|---|---|---|
| 4,160,204 A | | 7/1979 | Holmgren |
| 4,198,853 A | | 4/1980 | Graham et al. |
| 4,218,606 A | * | 8/1980 | Whitman, III ............. 219/121.6 |
| 4,676,091 A | * | 6/1987 | Schuster et al. .................. 73/38 |
| 5,013,403 A | | 5/1991 | Chase |

(Continued)

FOREIGN PATENT DOCUMENTS

| EP | 2469623 A1 | 6/2012 |
|---|---|---|
| WO | 2012117162 A1 | 9/2012 |

(Continued)

OTHER PUBLICATIONS

International Search Report for PCT/CA2014/000661 Nov. 27, 2014.

*Primary Examiner* — Tarifur Chowdhury
*Assistant Examiner* — Michael P Lapage
(74) *Attorney, Agent, or Firm* — Casio Schmoyer & Zervas

(57) ABSTRACT

Dual mounting head scanners measure the thickness of flexible moving porous webs and employ an air clamp on the operative surface of the lower head to maintain the web in physical contact with a measurement surface. As the web is held firmly by the clamp, the vacuum level that is established is indicative of the porosity of the membrane. As compressed air is supplied to a vacuum generator at a given operational pressure, the rate of airflow through the web can be inferred from the vacuum pressure measurements. The rate of airflow through the membrane and therefore the porosity of the membrane are related to the vacuum level. It is not necessary to measure the airflow through the membrane. From the vacuum pressure measurements, the membrane's permeability can also be determined by correlation to empirical data. Thickness measurements are effected by optical triangulation and inductive proximity measurements.

18 Claims, 4 Drawing Sheets

(56) References Cited

U.S. PATENT DOCUMENTS

| | | | |
|---|---|---|---|
| 5,087,313 A | 2/1992 | Duecker | |
| 5,094,535 A | 3/1992 | Dahlquist | |
| 5,166,748 A | 11/1992 | Dahlquist | |
| 5,728,930 A * | 3/1998 | Virta | 73/38 |
| 6,281,679 B1 | 8/2001 | King | |
| 6,450,009 B1 | 9/2002 | Hartikainen et al. | |
| 6,743,338 B2 | 6/2004 | Graeffe et al. | |
| 6,936,137 B2 | 8/2005 | Moeller | |
| 6,967,726 B2 | 11/2005 | King | |
| 7,515,281 B2 | 4/2009 | Loopstra | |
| 7,528,400 B2 | 5/2009 | Duck | |
| 7,829,136 B2 | 11/2010 | Saito et al. | |
| 7,892,399 B2 | 2/2011 | Graham et al. | |
| 8,192,864 B2 | 6/2012 | Takezawa et al. | |
| 8,388,094 B2 | 3/2013 | Rosati et al. | |
| 2003/0024301 A1* | 2/2003 | Graeffe et al. | 73/37.6 |
| 2003/0180154 A1 | 9/2003 | Yamazaki et al. | |
| 2009/0059244 A1* | 3/2009 | Hellstrom et al. | 356/630 |
| 2009/0260771 A1 | 10/2009 | Alev | |
| 2009/0260772 A1 | 10/2009 | Alev | |
| 2010/0078140 A1 | 4/2010 | Hughes | |
| 2013/0083332 A1 | 4/2013 | Heath et al. | |

FOREIGN PATENT DOCUMENTS

| | | |
|---|---|---|
| WO | WO2012/117162 A1 | 9/2012 |
| WO | 2013044358 A1 | 4/2013 |

* cited by examiner

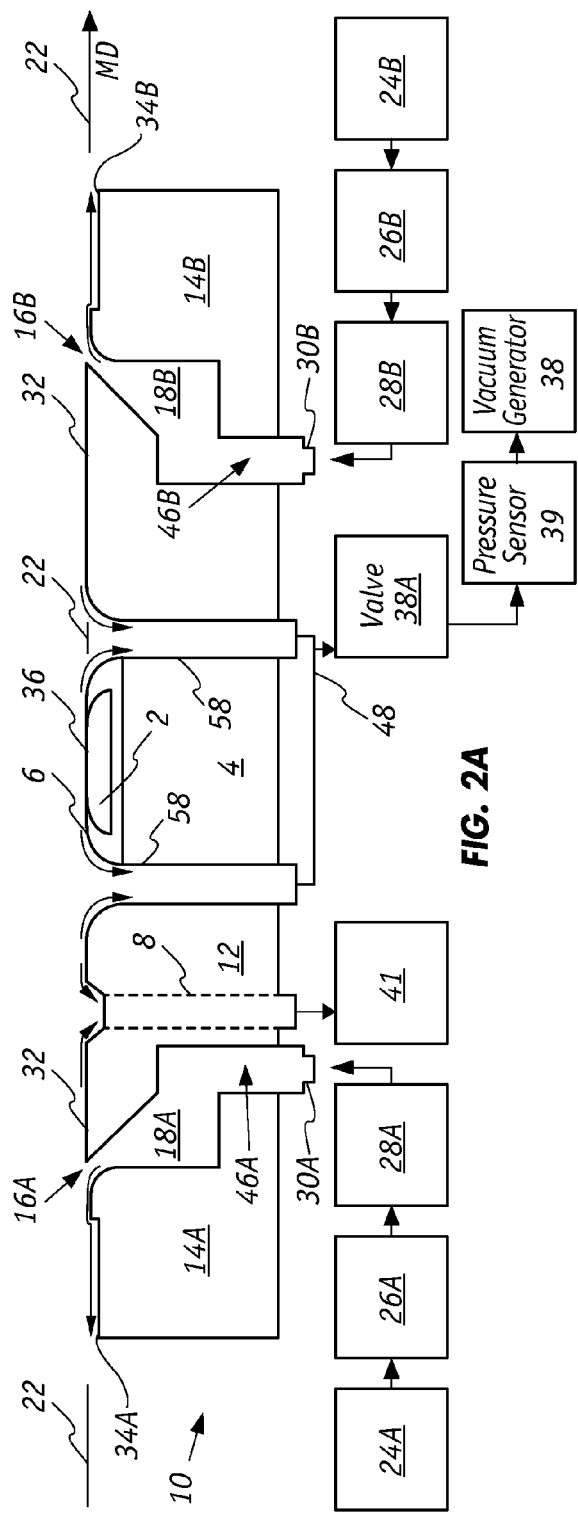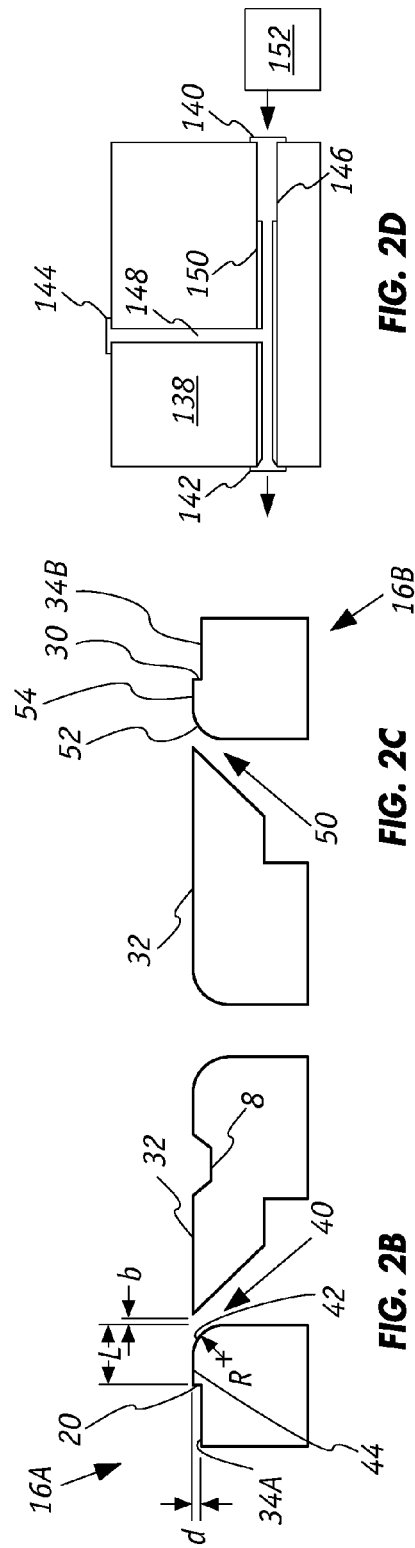

CO-LOCATED POROSITY AND CALIPER MEASUREMENT FOR MEMBRANES AND OTHER WEB PRODUCTS

FIELD OF THE INVENTION

The present invention relates generally to a dual mounting head scanner system for simultaneously measuring the thickness and porosity of a flexible continuous moving web. An air clamp and vacuum source assembly maneuvers the moving web into physical contact with a measurement surface that is incorporated in the operative surface of the lower head. Typically, an optical triangulation sensor measures the distance between the upper head and the upper surface of the web while a displacement sensor such as an inductive proximity sensor measures the distance between the upper head and measurement surface. The airflow through the web and thus the porosity of the membrane can be inferred from the vacuum pressure that is established by the air clamp.

BACKGROUND OF THE INVENTION

The thickness and porosity or permeability of web products such as paper and plastics are important product parameters. For example, lithium-ion battery separators, which are made of porous polymeric membranes, must have uniform thickness (typically to less than one micron) and meet specific electrolyte permeability standards. The art is desirous of developing reliable on-line techniques for measuring the thickness and calculating the permeability of web materials during production.

SUMMARY OF THE INVENTION

In the manufacture of web or sheet products such as plastic membranes used as separators in lithium-ion batteries, sensors that measure web properties are housed in enclosures that are scanned across the web as the membrane is produced. These opposite-facing enclosures are positioned on either side of the web, which is approximately centered in the gap formed between them. As the scanner moves laterally from one edge of the traveling web to the other, mechanical and thermal variations cause the distance between the two enclosures to change.

The precise positions of both sides of the web must be identified in order to make accurate dynamic web thickness measurements. With the inventive technique, the lower side of the moving web is held against a flat measurement surface. Subsequently, the distance from an opposing side on the upper enclosure to the exposed, visible upper side of the moving sheet is measured with an optical sensor, such as a laser triangulation device, while, simultaneously, the position from the upper enclosure to the measurement surface that is in contact with the sheet is measured, preferably with an electromagnetic induction sensor. The thickness of the web is the difference between the two distance measurements with a constant offset.

An air clamp or stabilizer and vacuum assembly subjects the moving flexible web, which is traveling in the machine direction, to forces sufficient to support and pull the web toward the measurement surface that is formed on an operative surface in the lower enclosure. In particular, suction forces generated by vacuum channels, which are in gaseous communication with a vacuum generator and that are configured adjacent the measurement surface, flatten the contour of the web and holds the web in physical contact against the measurement surface as the web passes over the measurement surface. The above-described two distance measurements are conducted as the moving web is held on the measurement surface thereby yielding accurate continuous web thickness measurements.

The present invention is based, in part, on the recognition that when the web is held firmly on the measurement surface by the vacuum of the air clamp, the vacuum level that is established is indicative of the porosity of the membrane. In particular, as compressed air is supplied to a vacuum generator at a given operational pressure, the rate of airflow through the web as it is being held can be inferred from the vacuum pressure measurements. With the inventive detector device, a good seal is established around a selected vacuum channel so that air entering the vacuum channel must travel through the web. In this fashion, the rate of airflow through the membrane is controlled, in part, by the vacuum level within the vacuum channel. The porosity of the membrane in turn is correlated to rate of airflow through the membrane. With the inventive technique, it is not necessary to measure the airflow through the membrane to ascertain its porosity. From the vacuum pressure measurements, the membrane's permeability to various substances can also be determined by correlation to empirical data using calibration techniques.

In one aspect, the invention is directed to a detector device, for measuring the porosity and thickness of a flexible continuous web that is moving in a downstream machine direction, which includes:

(a) a first mounting head disposed on a first side of the moving web and which has a reference surface;

(b) a second mounting head disposed on a second side of the moving web and which has an operative surface facing the second side of the web wherein the operative surface defines a measurement surface and has a web entry end and a web exit end that is downstream from the web entry end;

(c) a displacement sensor that determines a distance from the reference surface to the measurement surface;

(d) one or more channels that are disposed on the operative surface and that are in gaseous communication with a vacuum source so that the second side of the moving web is in vacuum engagement with the operative surface and the second side of the web comes into contact with the measurement surface as the web passes over the measurement surface;

(e) means for measuring the pressure in the one or more of the channels when the second side of the moving web is vacuum engaged to the operative surface;

(g) means for calculating the porosity of the moving web; and (f) means for calculating the thickness of the moving web.

In a preferred embodiment, the operative surface has a first inner channel that at least partially encircles the measurement surface and a second outer channel that is located up stream of the first inner channel. Each channel being in communication with a vacuum source. The suction in the second outer channel removes or strips off entrained gas (e.g., air) between the moving web and the operative surface. This ensures that as the web approaches in the machine direction toward the first inner channel that the web covers the outer perimeter of the first inner channel so as to establish a good seal so that the inner vacuum can measure the air flowing through the web.

In yet another aspect, the invention is directed to a method of measuring the porosity and thickness of a flexible continuous web that is moving in a downstream machine direction (MD) along a path that includes the steps of:

(a) maneuvering the continuous web through a dual scanner head that includes:
  (i) first mounting head disposed adjacent to a first side of the web, the first mounting head including:
    (A) a first operative surface facing the first side of the web; and
    (B) an optical sensor for measuring the distance from the optical sensor to the first side of the web; and
  (ii) a second mounting head disposed adjacent to the second side of the web, the second mounting head including:
    (A) a body having a second operative surface facing the second side of the web wherein the second operative surface defines a measurement surface wherein the first operative surface and the second operative surface define a measurement gap, that has a web entry end and a web exit end that is downstream from the web entry end, through which the continuous web travels;
    (B) an air stabilizer that supports the flexible continuous web as the web travels through the measurement gap; and
    (C) a first vacuum channel formed on the second operative surface that applies a suction force on the web to maintain the web in contact with the measurement surface as the web passes over the measurement surface;
  (iii) a displacement sensor that determines a displacement distance from the first operative surface to the measurement surface;
(b) measuring the displacement distance;
(c) measuring the distance between the first operative surface and the first side of the web;
(d) calculating the thickness of the moving web;
(e) measuring the pressure in the first vacuum as the web moves over the first vacuum; and
(f) calculating the porosity of the moving web based on the pressure measured in step (e) wherein the calculation of the porosity does not require measurement of airflow through the moving web.

BRIEF DESCRIPTION OF THE DRAWINGS

FIG. 2A is a cross sectional schematic view of the lower scanner head illustrating the measurement surface and vacuum channels on the operative surface of an air stabilizer and vacuum system to measure porosity;

FIGS. 2B and 2C are enlarged cross sectional views of Coanda nozzles;

FIGS. 2D and 2E illustrate two vacuum generators;

DETAILED DESCRIPTION OF THE PREFERRED EMBODIMENTS

Figure 1:
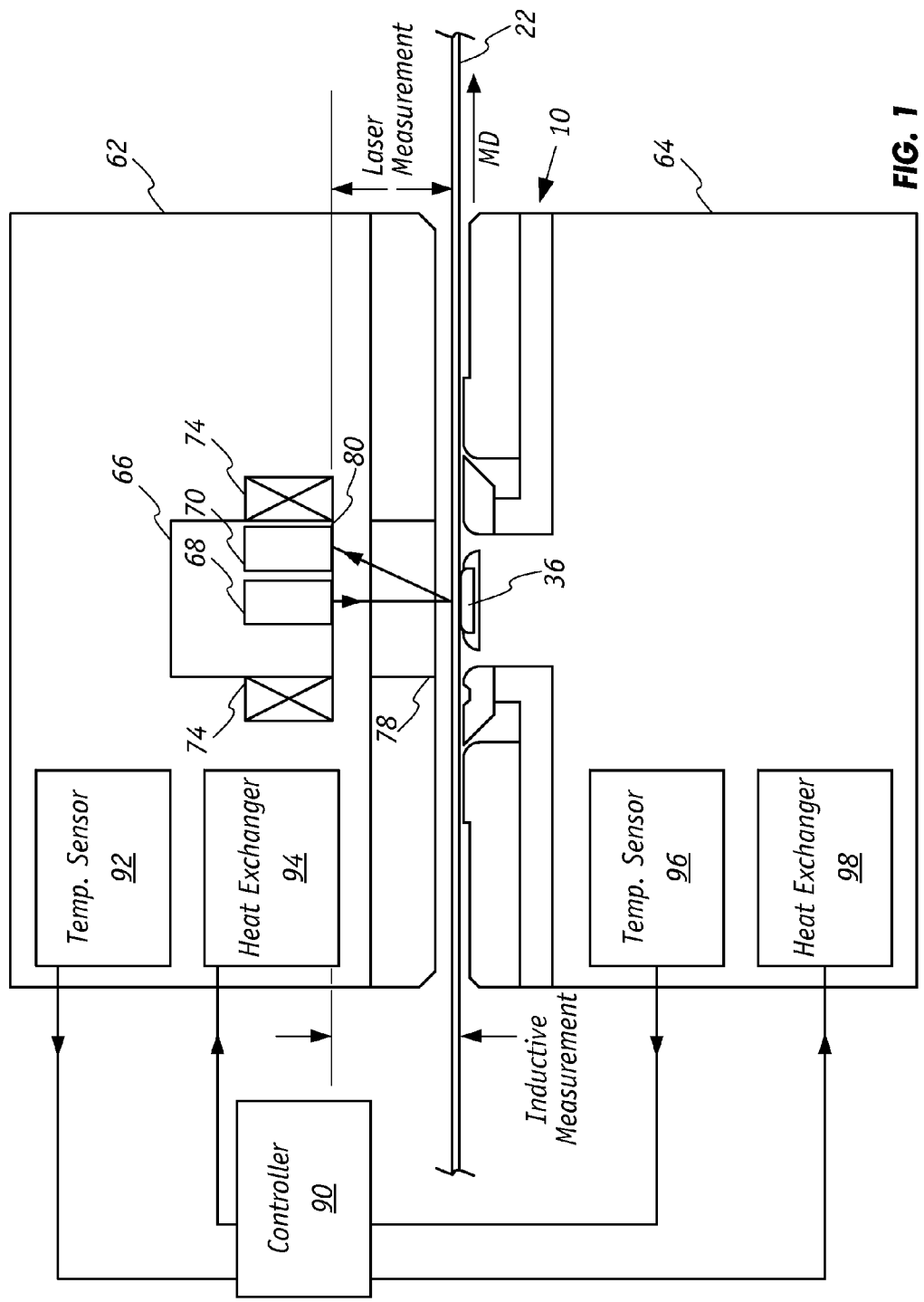
FIG. 1 is a cross sectional schematic view of a dual scanner head system employing the co-located caliper and porosity measurement sensors.

FIG. 1 illustrates a caliper and porosity sensor system that includes upper and lower sensing scanner heads 62 and 64, which are positioned on opposite sides of web or sheet 22. The two heads define a measurement gap and, if the measurements are to be performed in a scanning manner across the web in the cross direction, the heads are aligned to travel directly across from each other as they traverse the web which is moving in the machine direction (MD). The sensor system can be employed to continuously measure porous webs made of paper, plastics and the like, as further described herein.

In a preferred embodiment, upper head 62 includes a laser triangulation device 66 that gauges the perpendicular distance between a base surface 80 of device 66 to the top of moving web 22 as the web is in contact with measurement surface that is preferably configured as a zirconia disk or button 36. This operation being referred to as the laser measurement. Laser triangulation device 66 includes radiation source 68 and detector 70; incident radiation from source 68 passes through an aperture 78 in upper head 62 and detector 70 captures reflection radiation. The distance between base surface 80 and a measurement or interrogation spot on upper surface of the web 22 can be inferred by measuring the spot on the detector where the image is. Since the distance between detector 70 and source 68 is known, the distance between base surface 80 and the spot of the web can be calculated. In addition, upper head 62 includes a displacement measurement apparatus that measures the distance from the apparatus at base surface 80 to measurement surface 36 that is in contact with web 22 below. A preferred apparatus is an inductive-type sensor that has an RF or z-coil 74, which measures the distance from z-coil 74 to measurement surface 36 of lower head 64. Suitable z-coils consist of a metal wire that is preferably made of aluminum nitride. The laser triangulation sensor projects a beam onto the center of the zirconia button 36. The center of z-coil 74 preferably matches with the center of the zirconia button 36. Aside from employing triangulation, another method to measure the distance between the upper head and lower and the web uses chromatic confocal sensors which are described for example in U.S. Pat. No. 7,738,113 to Marx et al. and U.S. Pat. No. 8,212,997 to Xie, which are incorporated herein by reference.

As further illustrated in FIG. 1, lower head 64 incorporates an air clamp and vacuum assembly 10 which supports moving web 22 and which initially flattens the contour of the moving web as it approaches measurement surface 36 and then holds web 22 in contact with measurement surface 36 as web 22 passes over it. The heads 62 and 64 are typically fixed in positions so that the interrogations spots do not move in the machine direction even as the heads are scanned in the cross direction. The caliper of a moving sheet 22 that travels between two heads 62, 64 is determined by making the laser measurement, d (optical), and inductive measurement, d (inductive). Thereafter, the thickness (t) of sheet 22 is calculated as being the difference between the two measurements with a constant offset, that is: t=d (inductive)−d (optical)−C. The offset constant is determined by calibration that is preferably conducted by taking a zero measurement when the sensor is offsheet, that is, when there is no sheet between the heads.

The temperatures in the upper and lower heads can also be independently regulated with controller 90, which actuates heat exchangers 94 and 98 in response to signals from temperature sensors 92 and 96, respectively. The maintain accuracy the temperatures of z-coil 74 and laser triangulation device 66 can be independently controlled.

A feature of the present invention is that moving web 22 remains in contact with measurement surface 36 to ensure accurate and consistent thickness measurements. This is accomplished in part by employing an air clamp that supports and pulls the moving web toward measurement surface and one or more vacuum channels, which are disposed on the operative surface adjacent the measurement surface, which holds the moving web against the measurement surface.

Suitable air clamps or stabilizers include an operative surface and one or more nozzles that are disposed on the operative surface. As a moving web travels above the operative surface, gas jets from the nozzles establish pressure fields that support and maintain the moving web at a desired distance from the operative surface.

FIG. 2A illustrates an air clamp and vacuum assembly 10 that incorporates opposite-facing nozzles that are configured with backsteps to generate suction forces that are applied to a moving web 22. The assembly 10 includes a stainless steel body that is segmented into a central region 12, lateral region 14A and lateral region 14B. Central region 12 has an operative surface 32 that is situated between Coanda nozzles 16A and 16B, which are in gaseous communication with chambers 18A and 18B, respectively. Coanda nozzles 16A and 16B exhaust jets of gas in opposite directions toward surface 34A and 34B, respectively, which are downstream of the backstep features of nozzles.

Chamber 18A is connected to plenum chamber 46A which in turn is connected to a source of gas 24A via conduit 30A. The gas flow rate into plenum 46A can be regulated by conventional means including pressure controller 28A and flow regulator valve 26A. Plenum 46A essentially serves as a reservoir in which high pressure gas equilibrates before being evenly distributed along the length of Coanda nozzle 16A via chamber 18A. Similarly, chamber 18B is in gaseous communication with plenum chamber 46B, which is connected to a source of gas 24B via conduit 30B. Gas flowing into plenum 46B is regulated by pressure controller 288 and flow regulator valve 26B. Any suitable gas can be employed in gas sources 24A and 24B including for example, air, helium, argon, carbon dioxide.

Central region 12 includes a lower compartment 4 that houses hard ceramic disk 2 that is secured with epoxy in a depression 6 that has been milled out from the stainless body. A preferred material for the disk is zirconium dioxide. The planar, upper surface of disk 2 serves as the measurement surface 36. Encircling at least a portion of the outer perimeter of depression 6 is inner vacuum channel 58 and upstream from inner vacuum channel 58 is second vacuum channel 8. Vacuum channel 58 is connected to an air valve 38A, a pressure sensor 39 and a vacuum generator 38 via conduit 48. The pressure sensor 39 measures the pressure in vacuum channel 58 when the air valve 38A is open. Vacuum channel 8 is connected to a vacuum generator 41 which is usually set to a generate a higher suction force relative to that of vacuum generator 38 in order to remove any entrained air under the moving web 22.

Figure 2E:
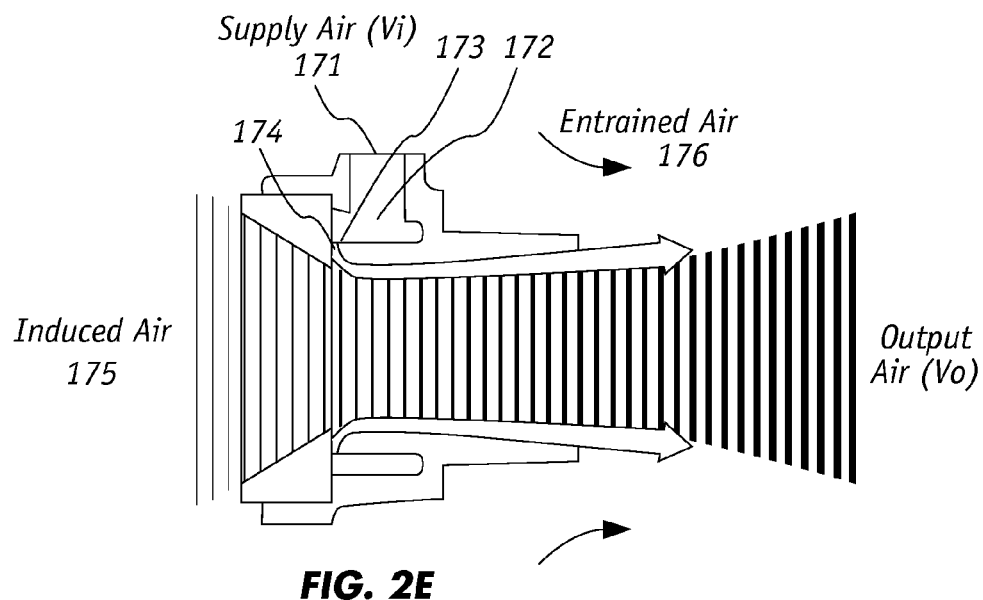

As shown in FIG. 2D, a vacuum generator preferably comprises a venturi vacuum pump 138 that has an air-inlet port 140, an air-discharge port 142, and a vacuum port 144. Channel 146 connects inlet port 140 to discharge port 142. As operational compressed air from air supply 152 is introduced through inlet port 140, the gas flows through channel 146 and passes through nozzle 150 whereupon channel 146 narrows. The narrowing of the channel results in the gas's speed increases, and because of the Venturi effect, its pressure decreases. A vacuum at vacuum port is established through channel 148. By measuring the vacuum in inner vacuum channel 58 (FIG. 2A) at a given operational pressure for the compressed air, air porosity of membrane 22 (FIG. 2A) can be inferred, as described herein. An alternate method of generating a vacuum in addition to the venturi vacuum pump is illustrated in FIG. 2E in which an air amplifier operates by using the Coanda effect to create a low pressure volume from a high pressure supply. In this configuration, an air amplifier directs air from the inlet port 171 to a circumferential plenum 172. A circumferential nozzle 174 throttles the flow and directs it towards a curved surface 173 where it is directed towards the outlet port by the Coanda effect. This generates a low pressure region drawing flow from the inlet port 175. Entrained air 176 flows along the perimeter.

As illustrated in FIG. 2B, Coanda nozzle 16A has a Coanda slot 40 between upper surface 44 and operative surface 32 which are preferably coplanar. Coanda slot 40 has a curved convex surface 42 on its downstream side, with a radius of curvature (R) typically ranging from about 1.0 mm to about 10 mm. Airflow from the Coanda slot 40 follows the trajectory of the curved surface 42. The term "backstep" is meant to encompass a depression on the stabilizer surface located a distance downstream from Coanda slot 40 configured so that gas has room to expand to create the large, low pressure area. The combination of the Coanda slot and backstep generates an amplified suction force and an extensive air bearing.

Backstep 20 is most preferably configured as a 90 degrees vertical wall. Preferably. Coanda slot 40 has a width (b) of about 3 mils (76 μm) to 5 about mils (127 μm). The distance (d) from the upper surface 44 to lower surface 34A, which are preferably parallel to each other, is preferably between about 100 to 1000 μm. Preferably the backstep location (L) is about 1 mm to about 6 mm and preferably about 2 mm to 3 from Coanda slot 40.

Similarly, as shown in FIG. 2C, Coanda nozzle 16B has a Coanda slot 50 between upper surface 54 and coplanar operative surface 32. Coanda slot 50 has a curved surface 52 on its downstream side. The dimensions of structures forming Coanda nozzle 168, including backstep 30 and lower surface 34B, can be the same as those for Coanda nozzle 16A.

Referring to FIG. 2A, the air clamp and vacuum assembly 10 is positioned underneath a web of material 22 which is moving from left to right relative to the assembly, this direction from the web entry end to the web exit end through the measurement gap being the downstream machine direction (MD) and the opposite direction being the upstream machine direction. The cross direction (CD) is transverse to the MD. Operative surface 32 and measurement surface 36 are preferably not coplanar. The measurement surface is raised between 0.005 in. (0.127 mm) to 0.120 in. (0.508 mm) above the operative surface. The middle part of web 22 that is passing over operative surface 32 is not shown for clarity.

The contour of web 22 as it travels over operative surface 32 is manipulated with the air clamp and vacuum channels. In a preferred application, the profile of web 22 is substantially planar as in approaches measurement surface 36. The sub-ambient pressure generated by vacuum channel 58 urges web 22 toward and into physical contact with measurement surface 36. The higher the vacuum levels, the greater the suction force imparted on moving web 22. The thickness measurement devices of the present invention can be incorporated into on-line dual head scanning sensor systems.

Figure 3:
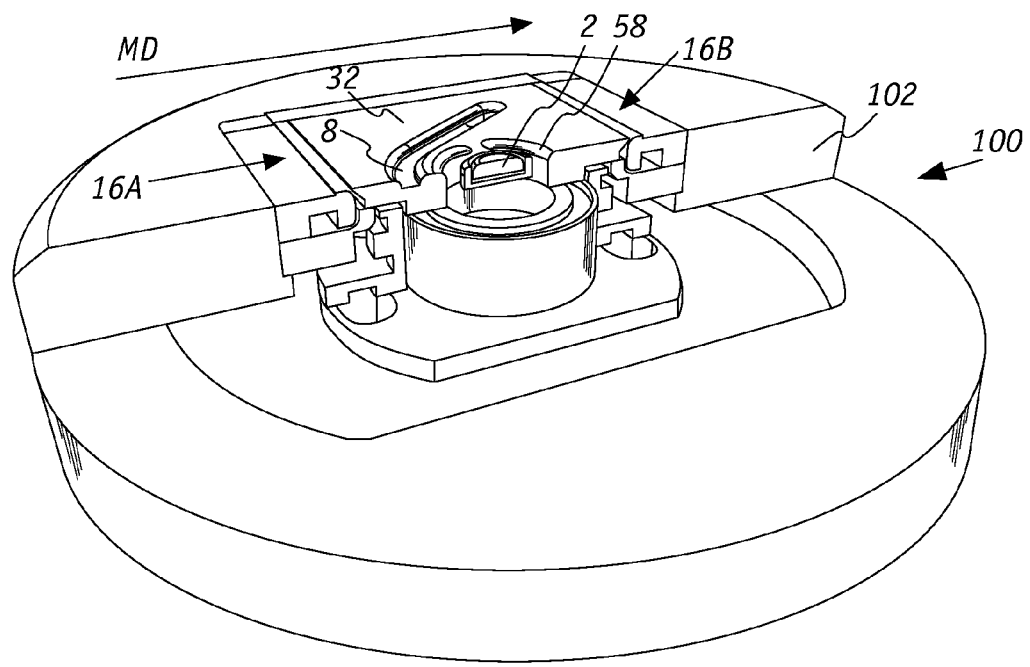
FIG. 3 shows a perspective cross sectional view of the web thickness measurement device as part of a sensor head.
Figures 4, 5:
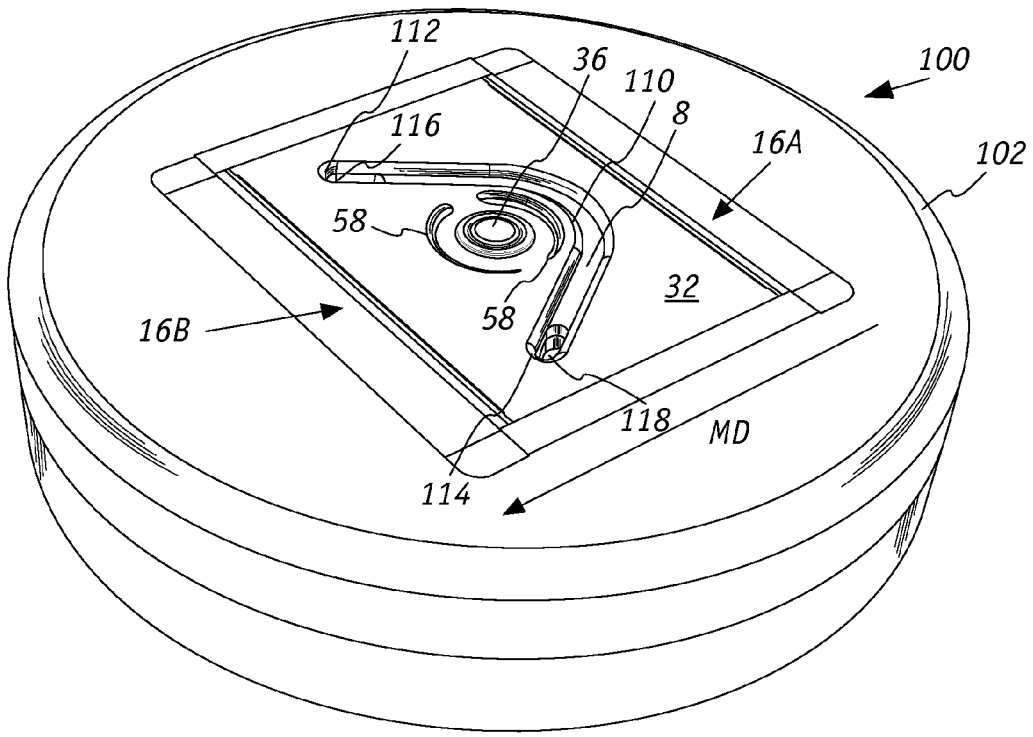
FIG. 4 shows a perspective view of the operative surface of the measurement device as part of the sensor head.
FIG. 5 is a diagram of a system employing process measurements to calculate the caliper and porosity of the web.

FIGS. 3 and 4 show an air clamp and vacuum assembly that is incorporated into a recess compartment within substrate 102 that is a part of lower head 100 of a dual scanning sensor. The upper surface of disk 2 serves as measurement surface 36, which is located in the middle of operative surface 32 between Coanda nozzles 16A and 16B. Inner vacuum channels 58 form a ring structure that partially encircles measurement surface 36 and outer vacuum channel 8 and that has a curved, arch-shaped configuration that partially encircles inner vacuum channels 67, 59. As shown in FIG. 3, vacuum channel 8 has a proximal end 110 and distal ends 112 and 114 where gas vacuum ports 116 and 118, respectively are located. Substrate 102 is positioned so that as a web product travels toward operative surface 32 in the machine direction, the web after traveling over Coanda nozzle 16A encounters the forces generated by vacuum channels 8 and 58. The web's contour is flattened as it approaches measurement surface 36 and is held thereon as it passes over the surface.

When employed for measuring porous membranes, in one embodiment, the distance between nozzles 16A and 16B is about 50 mm and the length of each nozzle along the cross direction is about 75 mm. The zirconium disk 2 has a diameter of 0.375 inches (0.95 cm). The straight Coanda nozzles 16A and 16B which are located at the web entrance and exit ends of measurement surface 32, respectively, have linear slots that are perpendicular to the machine direction.

The present invention is particularly suited for calculating the caliper and permeability of plastic membranes used as separators in lithium-ion batteries, which consists of anode, cathode, separator there-in-between, and lithium electrolyte that includes lithium salt dissolved in an organic solvent. The separator is a barrier through which the lithium ions migrate back and forth during charging and discharging of the battery. The separator must exhibit sufficient structural integrity and permeability to lithium ions in the electrolyte. A suitable material is NAFION, which is a synthetic copolymer membrane available from Du Pont (Wilmington Del.). Co-located porosity and caliper measurements can also be made for other plastic membrane materials that include, for instance, polyethylene, polypropylene, polyethylene terephthalate, polytetrafluoroethylene and polyvinyl chloride.

The vacuum pressure measurements P can be used to estimate the porosity and permeability of the web. To achieve this, normalized pressure Pnorm measurements are computed. Referring to FIG. 2A, normalization of the pressure takes into account the maximum vacuum pressure that can be generated by the vacuum pump 38. Normalization is also used to limit the effect of dirt accumulation in the vacuum channel 58 in the porosity and permeability measurements. A maximum vacuum pressure Pmax is measured periodically, for example when the scanner head is in an offsheet position, by closing air valve 38A. A measurement of the amount of dirt in vacuum channel 58 is performed by measuring the pressure Pdirt using the pressure sensor 39 when the scanner head is offsheet and no web is present near operative surface 32 and measurement surface 36. The normalized pressure Pnorm is defined as: Pnorm=(P−Pmax)/(Pdirt−Pmax). The normalized pressure depends on the porosity and thickness of web 22. The more porous the material forming the web, the lower the vacuum level (the higher the Pnorm). A method of correlating pressure measurements to porosity is to create a library of calibration standards by producing membranes over a range of porosities that are then measured and assigned porosity values in the laboratory. Another method is to develop models based on the data. The membranes with their known porosities are then subject to thickness and porosity measurements with the device of the present invention to establish the required correlations. Each membrane material of interest will require a different set of calibration standards. These correlations are subsequently used to relate thickness and porosity measurements to actual porosities.

An analogous procedure can be used to create calibration standards to relate measured thickness and porosity measurements to a material's permeability to lithium-ions in electrolyte. A web material's permeability to substance(s) in general can be so established.

FIG. 5 depicts a process for controlling the manufacture of porous membranes or similar webs by continuously measuring the caliper and the porosity of the web. Digitized signals 160, 162 representing the caliper of the membrane 22 and pressure within inner vacuum channel 58 (FIG. 2A), respectively, are fed to a computer 164. Memory 166 includes data from calibration measurements that correlate the vacuum pressure to the air porosity of the membrane. In the case where the membrane is to be used as a separator in lithium ion batteries, the calibration data can further correlate the pressure to its permeability to lithium ions in an electrolyte.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A detector device for measuring a porosity and thickness of a flexible continuous web that is moving in a downstream machine direction, which comprises:
    (a) a first mounting head disposed on a first side of the moving web and which has a reference surface;
    (b) a second mounting head disposed on a second side of the moving web and which comprises a body having an operative surface facing the second side of the web wherein the operative surface defines a measurement surface and has a web entry end and a web exit end that is downstream from the web entry end;
    (c) a displacement sensor positioned in the first mounting head that determines a distance from the reference surface to the measurement surface;
    (d) one or more channels that are disposed in the operative surface and that are in gaseous communication with a vacuum source so that the second side of the moving web is in vacuum engagement with the operative surface and the second side of the web comes into contact with the measurement surface as the web passes over the measurement surface;
    (e) means for measuring the pressure in the one or more of the channels when the second side of the moving web is vacuum engaged to the operative surface;
    (g) means for calculating the porosity of the moving web; and
    (f) means for calculating the thickness of the moving web.

2. The detector device of claim 1 wherein the vacuum source comprises a vacuum generator that includes a source of compressed gas that delivers compressed air to a nozzle that forms a high speed low pressure jet thereby pulling a vacuum from a vacuum port that is in gaseous communication with the one or more channels, wherein the means for calculating the porosity of the moving web does not require measurements of gas flow rate through the one or more channels.

3. The detector device of claim 1 which comprises means for positioning the moving web that includes an air-clamp that pulls the moving web toward measurement surface.

4. The detector device of claim 3 wherein the air-clamp comprises a first channel that is disposed in the operative surface and which at encircles at least part of the perimeter of the measurement surface, wherein sub-ambient pressure from the first channel holds the moving web against the measurement surface.

5. The detector device of claim 4 wherein the first channel defines a first region that is upstream of the measurement surface and a second region that is downstream of the measurement stream.

6. The detector device of claim 5 wherein the air-clamp further comprises a second channel that is disposed on the operative surface and which at least partially encircles the first channel and the second channel which has one or more vacuum ports located downstream from the first channel.

7. The detector device of claim 6 wherein the first channel is connected to a first vacuum source and the second channel is connected to a second vacuum source that generates a higher suction than that of the first vacuum source.

8. The detector device of claim 6 wherein the second channel removes entrained gas that is between the moving web and the operative surface.

9. The detector device of claim 3 further comprising a first linear Coanda nozzle that is located on the operative surface at a web entrance and spaced from the air-clamp and a second linear Coanda nozzle on the operative surface at the web exit and spaced from the air-clamp wherein the first and second linear Coanda nozzles establish low pressure zones from the Coanda nozzles to pull the web so it can be engaged by the air clamp.

10. The detector device of claim 9 wherein the optical sensor comprises a source of incident radiation that is directed toward the moving web and on an interrogation area on the first side of the moving web and a detector for detecting reflected radiation from the interrogation area.

11. The detector device of claim 1 comprising an optical sensor, positioned in the first mounting head, for measuring the distance from the optical sensor to the first side of the moving web at the measurement surface.

12. The detector device of claim 1 wherein the web comprises a porous polymeric membrane.

13. A method of measuring a porosity and thickness of a flexible continuous web that is moving in a downstream machine direction (MD) along a path that comprises the steps of:
   (a) maneuvering the continuous web through a dual scanner head that comprises:
      (i) first mounting head disposed adjacent to a first side of the web, the first mounting head including:
         (A) a first operative surface facing the first side of the web; and
         (B) an optical sensor for measuring a distance from the optical sensor to the first side of the web; and
      (ii) a second mounting head disposed adjacent to the second side of the web, the second mounting head comprising:
         (A) a body having a second operative surface facing the second side of the web wherein the second operative surface defines a measurement surface wherein the first operative surface and the second operative surface define a measurement gap, that has a web entry end and a web exit end that is downstream from the web entry end, through which the continuous web travels;
         (B) an air stabilizer that supports the flexible continuous web as the web travels through the measurement gap; and
         (C) a first vacuum channel formed on the second operative surface that applies a suction force on the web to maintain the web in contact with the measurement surface as the web passes over the measurement surface;
      (iii) a displacement sensor that determines a displacement distance from the first operative surface to the measurement surface;
   (b) measuring the displacement distance with the displacement sensor;
   (c) measuring a distance between the first operative surface and the first side of the web with the optical sensor;
   (d) calculating the thickness of the moving web;
   (e) measuring a pressure in the first vacuum as the web moves over the first vacuum; and
   (f) calculating the porosity of the moving web by:
      (i) referring to a library of calibration standards on the basis of the pressure measured in step (e) or
      (ii) applying a model to the pressure measured in step (e).

14. The method of claim 13 wherein the web is a porous polymeric membrane.

15. The method of claim 13 wherein the porosity that is calculated is further correlated to a permeability of the web material to lithium ion electrolytes.

16. The method of claim 13 wherein the porosity that is calculated is further correlated to a permeability of the web material to a substance that is selected from the group consisting of polyethylene, polypropylene, polyethylene terephthalate, polytetrafluoroethylene and polyvinyl chloride.

17. The method of claim 13 wherein the suction source comprises a vacuum generator that includes a source of compressed gas that delivers compressed air to a nozzle that forms a high speed low pressure jet thereby pulling a vacuum from a vacuum port that is in gaseous communication with the first vacuum channel, wherein calculating the permeability of the moving web does not require measurements of gas flow rate through the first vacuum channel.

18. The method of claim 13 wherein the second mounting head further comprises a second vacuum channel that is disposed on the operative surface and which at least partially encircles the first vacuum channel and the second channel which has one or more vacuum ports located downstream from the first vacuum channel.

* * * * *